United States Patent
Tiedtke et al.

(10) Patent No.: US 12,428,665 B2
(45) Date of Patent: Sep. 30, 2025

(54) DEVICE AND METHOD FOR IMMOBILISING BIOMOLECULES USING MAGNETIC PARTICLES

(71) Applicant: QIAGEN GmbH, Hilden (CH)

(72) Inventors: Hans-Jürgen Tiedtke, Bonn (DE); Harald Quintel, Steckborn (CH); Konstantin Lutze, Uerikon (CH)

(73) Assignee: QIAGEN GmbH, Hilden (CH)

( * ) Notice: Subject to any disclaimer, the term of this patent is extended or adjusted under 35 U.S.C. 154(b) by 332 days.

(21) Appl. No.: 16/643,183

(22) PCT Filed: Apr. 13, 2018

(86) PCT No.: PCT/EP2018/059543
§ 371 (c)(1),
(2) Date: Feb. 28, 2020

(87) PCT Pub. No.: WO2019/057345
PCT Pub. Date: Mar. 28, 2019

(65) Prior Publication Data
US 2020/0181684 A1 Jun. 11, 2020

Related U.S. Application Data

(60) Provisional application No. 62/562,647, filed on Sep. 25, 2017.

(51) Int. Cl.
*B01L 3/00* (2006.01)
*B03C 1/01* (2006.01)
(Continued)

(52) U.S. Cl.
CPC ......... *C12Q 1/6806* (2013.01); *B01L 3/5085* (2013.01); *B03C 1/01* (2013.01);
(Continued)

(58) Field of Classification Search
CPC ............ C12Q 1/6806; C12Q 2563/143; B01L 3/5085; B01L 2200/0668; B01L 2400/043;
(Continued)

(56) References Cited

U.S. PATENT DOCUMENTS 5,466,574 A * 11/1995 Liberti .................... B03C 1/035
                                                    435/7.5
6,136,182 A * 10/2000 Dolan .................... B03C 1/025
                                                    436/526
(Continued)

FOREIGN PATENT DOCUMENTS

CN 101027558 A1 8/2007
CN 102245770 A 11/2011
(Continued)

OTHER PUBLICATIONS

International Search Report issued Jun. 29, 2018 in corresponding International Patent Application No. PCT/EP2018/059543, filed Apr. 13, 2018 (with English Translation).
(Continued)

*Primary Examiner* — Paul S Hyun
(74) *Attorney, Agent, or Firm* — Global IP Counselors, LLP

(57) ABSTRACT

A device for the reversible immobilization of biomolecules by magnetic particles includes a container. The container is configured to be filled with a liquid containing biomolecules and a magnet. The magnet is arranged on the container in such a way that magnetic particles arranged in the container and to which the biomolecules are capable of being immobilized, are configured to be fixed in the container. An inhomogeneous magnetic field is configured to act on the magnetic particles disposed in the container and is capable of being generated by the arrangement of the magnet, so that
(Continued)

the magnetic particles are arranged in a structured manner by the influence of the inhomogeneous magnetic field.

15 Claims, 6 Drawing Sheets

(51) Int. Cl.
| | | |
|---|---|---|
| *B03C 1/02* | (2006.01) | |
| *B03C 1/033* | (2006.01) | |
| *B03C 1/28* | (2006.01) | |
| *C12N 15/10* | (2006.01) | |
| *C12Q 1/6806* | (2018.01) | |

(52) U.S. Cl.
CPC .............. *B03C 1/02* (2013.01); *B03C 1/0332* (2013.01); *B03C 1/0335* (2013.01); *B03C 1/288* (2013.01); *C12N 15/1013* (2013.01); *B01L 2200/0668* (2013.01); *B01L 2300/0829* (2013.01); *B01L 2400/043* (2013.01); *B03C 2201/18* (2013.01); *B03C 2201/26* (2013.01)

(58) Field of Classification Search
CPC ....... B03C 1/01; B03C 1/0332; B03C 1/0335; B03C 1/288; B03C 2201/18; B03C 2201/26; C12N 15/1013; G01N 33/54326; G01N 35/00
See application file for complete search history.

(56) References Cited

U.S. PATENT DOCUMENTS

| | | | |
|---|---|---|---|
| 6,413,420 B1 | | 7/2002 | Foy |
| 2002/0079998 A1* | | 6/2002 | Blange .................... B03C 1/288 |
| | | | 335/302 |
| 2003/0127396 A1* | | 7/2003 | Siddiqi ................. B03C 1/0335 |
| | | | 210/695 |
| 2008/0206099 A1* | | 8/2008 | Aruga .................... B03C 1/288 |
| | | | 422/68.1 |
| 2012/0149132 A1* | | 6/2012 | Toyoshima ........ G01N 35/0098 |
| | | | 436/547 |
| 2016/0108392 A1 | | 4/2016 | Stelling |

FOREIGN PATENT DOCUMENTS

| | | | | |
|---|---|---|---|---|
| DE | 19525654 A1 | | 1/1997 | |
| EP | 1065001 A1 * | | 1/2001 | .......... B01J 19/0046 |
| JP | 2004283738 A | | 10/2004 | |
| JP | 2005233931 A | | 9/2005 | |
| JP | 2011180111 A | | 9/2011 | |
| JP | 2013223820 A | | 10/2013 | |
| JP | 2014054633 A | | 3/2014 | |
| JP | 2016117032 A | | 6/2016 | |
| WO | 92/05443 A1 | | 4/1992 | |
| WO | 2016/061285 A1 | | 4/2016 | |
| WO | 2016063690 A1 | | 4/2016 | |

OTHER PUBLICATIONS

Peng Han, et al., "Design and Fabrication of a Hybrid HTS Magnet for 150 kJ SMES", Journal of Fusion Energy, Dec. 1, 2014, XP055484758, pp. 759-764.

Xavier Le Guezennec, et al., "Improving Bead-Based Multiplexing in Bodily Fluids" Genetic Engineering & Biotechnology News, vol. 36, No. 2, Jan. 15, 2016, XP055484818, pp. 1-4.

D. Humphries, et al., "New High Performance Hybridg Magnet Plates for DNA Separation and Bio-Technology Applications", Lawrence Berkeley National Laboratory Report: LBNL-56017, Aug. 2, 2004, pp. 1-12.

Japanese Office Action issued Sep. 2, 2022 in corresponding Japanese Application No. 2020-515183.

\* cited by examiner

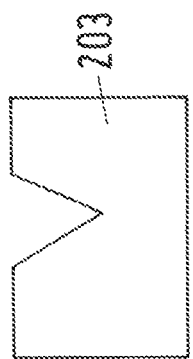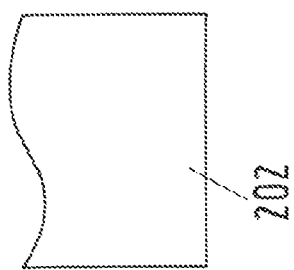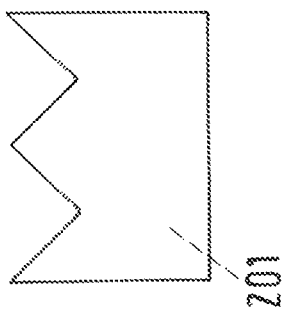
Fig.2

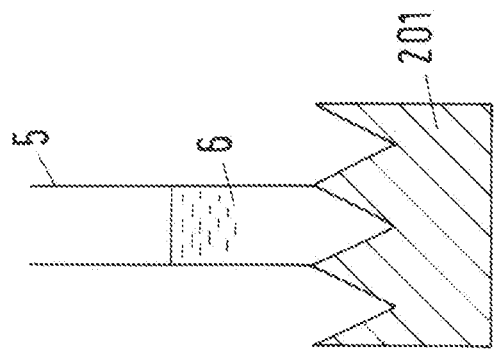
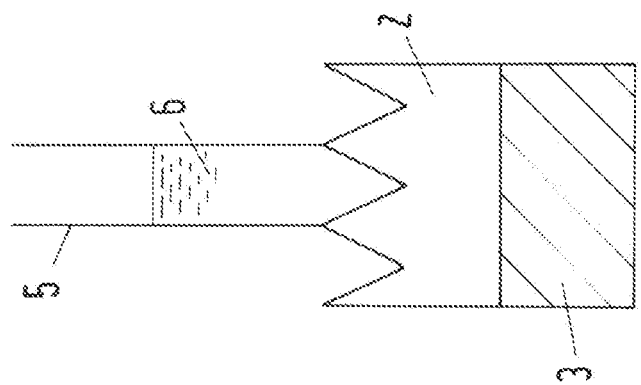
Fig. 3

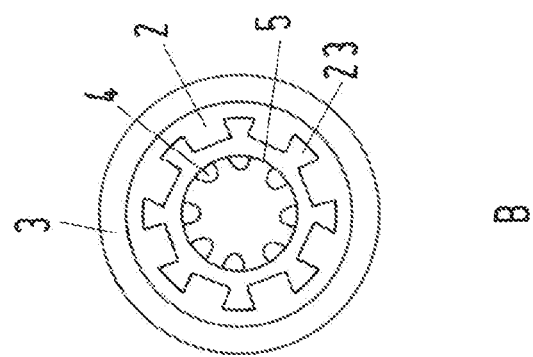
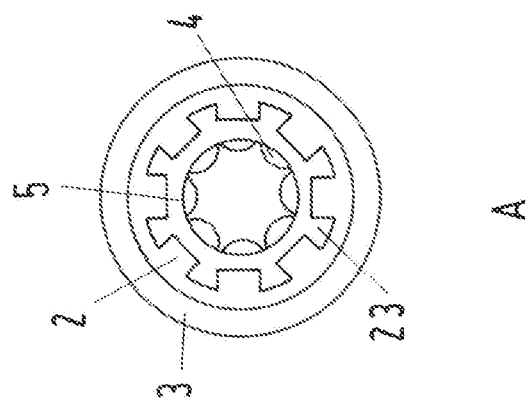
Fig. 6

DEVICE AND METHOD FOR IMMOBILISING BIOMOLECULES USING MAGNETIC PARTICLES

CROSS-REFERENCE TO RELATED APPLICATION

This application is a U.S. National Stage application of International Application No. PCT/EP2018/059543, filed Apr. 13, 2018, which claims priority to U.S. Provisional Patent Application No. 62/562,647, filed Sep. 25, 2017, the contents of each of which are hereby incorporated herein by reference.

BACKGROUND

Field of the Invention

The invention relates to a device for the reversible immobilization of biomolecules. The invention further relates to a method for the reversible immobilization of biomolecules. The invention further relates to an apparatus for the automated processing of biomolecules comprising a device for the reversible immobilization of biomolecules.

Background Information

Many methods for the purification of DNA and other biomolecules are known in the state of the art. One type of purification is DNA extraction, in which the DNA is precipitated in a nonpolar environment. DNA can also be purified by centrifugation, e.g. after cell disruption, or by electrophoretic methods.

Biomolecules can also be synthesized and purified by immobilization on an insoluble carrier. Common substrates for immobilizing biomolecules are glass and other less common substrates such as gold, platinum, oxides, semiconductors and various polymer substrates.

Since manual purification and processing of numerous operations requires too much time, the processes today are fully automated. So-called "magnetic particles" play an important role in the automation of laboratory methods. "Magnetic bead-based clean-up" and "magnetic bead-based normalization" are widely used methods for immobilization, purification and concentration adjustment of nucleic acids. Typical fields of application of these methods are sample preparation in the context of DNA sequencing or DNA detection (e.g. by PCR, polymerase chain reaction).

SUMMARY

In the state of the art, the magnetic particles are typically held in the container by ring magnets which enclose a container. This allows a solution with impurities to be pipetted off, while the magnetic particles with the bound biomolecules remain in the container.

The magnetic particles were developed in 1995 at the Whitehead Institute for the purification of PCR products. The magnetic particles are mostly paramagnetic and can consist of polystyrene, which is coated with iron. Various molecules with carboxyl groups can then be attached to the iron. These carboxyl groups can reversibly bind DNA molecules. In doing so, the DNA molecules are immobilized.

Processes with magnetic particles usually comprise the following steps. First, the PCR products are bound to the magnetic particles. Subsequently, the magnetic particles with the attached PCR products are separated from impurities (this step is realized e.g. by pipetting off the solution from the solid). The magnetic particles with the attached PCR products are then washed. After washing, the PCR products are eluted from the magnetic particles and transferred to a new plate.

In fully automated processes, the necessary reagents are automatically pipetted to the sample after the starting material has been introduced in an isolation process and are removed again by means of a pipette tip. The magnetic particle-bound nucleic acids are collected at the bottom and at the edge of the cavities and, depending on the routine, again dissolved by optimized pipetting. Finally, the DNA or RNA is eluted into separate vessels with lids for direct storage or further applications.

Adsorption methods are also known in the state of the art, in which DNA is bonded to silica gel in a slightly acidic environment, for example.

One of the most important processes for the synthesis, normalization and purification of biomolecules is the process with magnetic particles. Here the biomolecules are bound to the surface of the magnetic particles. The magnetic particles are then fixed by means of a magnet and the solution, which contains by-products and impurities, can be easily separated. The biomolecules can thus be purified and isolated quickly and easily. The advantage of magnetic globules is that the globules can move freely in the test batch, which is important for the binding steps. If, for example, you want to remove the liquid from the container in a washing step, you simply hold a magnet to the container and can then separate the liquid.

The magnetic particles are small para- or ferromagnetic globules, which are coated with different materials that provide the required properties. Nickel particles coated with a plastic are often used.

For example, DNA probes and genes can also be synthesized in automated solid phase methods. DNA strands, like polypeptides, can be synthesized by sequentially attaching activated monomers to a growing chain bound to an insoluble matrix (magnetic particles). Protected phosphoramidites can be used here as activated monomers.

This procedure allows the isolation of highly pure biomolecules with excellent yields. The underlying process of magnetic particle separation can be carried out fully automatically in the cavities of the extraction containers used.

In fully automated processes, the necessary reagents are automatically pipetted to the sample after the starting material has been introduced in the isolation process and are removed again by means of pipettes, for example. The magnetic particle-bound nucleic acids are collected at the bottom and at the edge of the cavities and, depending on the routine, again dissolved by optimized pipetting. Finally, the DNA or RNA is eluted into separate vessels with lids for direct storage or further applications.

In the state of the art, the magnetic particles are typically held in the container by ring magnets which enclose the container. As a result, the magnetic particles arrange themselves in a ring-shaped manner in the inner container.

It has been found that a significant disadvantage of the state of the art is that the magnetic particles in the container also arrange themselves in a ring-shaped manner due to the use of ring magnets. This not only makes it more difficult to remove the liquid, but it also means that there is still a liquid residue on the solid ring that cannot be removed. The incomplete removal of the liquid reduces the cleaning efficiency and the usable volume after elution.

One object of the invention is therefore to provide a device for the immobilization of biomolecules, a method for the reversible immobilization of biomolecules and an apparatus for the automated processing of biomolecules with a device for the immobilization of biomolecules, which avoid the adverse effects known from the state of the art.

This object is met by a device for the reversible immobilization of biomolecules with the features described herein, by a method for the reversible immobilization of biomolecules with the features described herein, and by an apparatus for the automated processing of biomolecules comprising a device for the reversible immobilization with the features described herein.

According to the invention, a device for the reversible immobilization of biomolecules by magnetic particles is proposed. This device comprises a container which can be filled with a liquid containing biomolecules and a magnet. The magnet is arranged on the container in such a way that magnetic particles, which can be arranged in the container, and to which the biomolecules can be immobilized, in particular can be reversibly immobilized, can be fixed in the container. An inhomogeneous magnetic field acting on the magnetic particles located in the container can be generated by the arrangement of the magnet. The magnetic particles can be arranged in a structured manner by the influence of the inhomogeneous magnetic field.

It is essential for the invention that the arrangement of the magnet generates inhomogeneity in the magnetic field. As a result, an inhomogeneous magnetic field acting on the magnetic particles located in the container is generated by the arrangement of the magnet, so that the liquid can flow off more easily from the magnetic particles by the structured arrangement of the magnetic particles in the inhomogeneous magnetic field. If the magnetic particles, controlled by the inhomogeneous magnetic field, arrange themselves in isolated islands on a container wall, the liquid can simply flow off between the magnetic particles and the liquid can therefore be removed from the container more easily.

Within the framework of the present invention, the arrangement of the magnet can be understood as a wide variety of designs. The arrangement of the magnet refers to the function of generating such an inhomogeneous magnetic field, which acts on the magnetic particles in the container, so that the magnetic particles arrange themselves in a structure according to the invention on the container wall. By diverting a magnetic flux density of the magnet, the magnetic particles arrange themselves in the container in such a way that the liquid can flow off more easily and can be removed more easily. The term "structure according to the invention" refers to a structure which allows the liquid to flow off more easily from the magnetic particles in the container. Thus, for example, the arrangement of magnetic particles in isolated islands can be understood as "structure according to the invention" or "structured arrangement", but the arrangement is not limited to this. The magnetic particles can also arrange themselves pyramidally or in grooves, for example. All the structured arrangements of the magnetic particles on the container wall described above allow the liquid to run off easily at or between the magnetic particles. To give examples of the design of the arrangement of the magnet, the following are various ways of arranging the magnet. Within the framework of the invention, the arrangement of the magnet can be understood as a special form of the magnet, whereby the form can refer to the external design of a permanent magnet or to the winding of a coil in an electromagnet. Furthermore, the arrangement of the magnet can be understood as a magnetically conductive module, with which the magnetic flux density is changed and thus an inhomogeneous magnetic field is generated. The arrangement of the magnet can also be understood as the arrangement of several magnets around the container at a predeterminable distance (distance from the container and distance between the magnets), so that a resulting magnetic field in form of the inhomogeneous magnetic field acts on the magnetic particles in the container. Here the resulting inhomogeneous magnetic field acts more strongly on the magnetic particles in some areas and less strongly on the magnetic particles in others. Of course, the same effect occurs with the other arrangements, since the magnetic field in some areas of the container acts more strongly on the magnetic particles in the container due to the magnetically conductive module and the form of the magnet. These possibilities are explained in more detail in the following description, as well as in the description of the figures. It should be noted once again that structured arrangement do not mean ring-shaped or similar arrangements of magnetic particles known from the state of the art.

The magnet may also be movably arranged on the container in such a way that the magnetic particles can move freely in the container during a reaction step and are fixed in place by changing the magnet position in the container during a washing step. In particular, the magnet may be movable such that the magnet is arranged in a first position on the container and fixes the magnetic particles and, by moving the magnet into a second position on or around the container, the magnetic particles become movable. Of course, in an automated device, for example, the container can also be moved relative to the magnet to achieve the same effect.

Within the framework of this invention, the term biomolecule refers to DNA, RNA, nucleic acids, proteins, start sequences for biomolecules, monomers or other biologically active molecules.

In the following, a washing step is generally a process step in which the liquid is discharged from the containers by actuating the valve and in which the impurities of magnetic particles with the attached biomolecules are separated. A washing step can also include washing with a washing solution (water or others).

In the following, a reaction step is generally a process step in which the biomolecules bound to the magnetic particles are converted, bound to the particles or extended (chain extension, e.g. PCR "polymerase chain reaction").

In the following, an impurity is generally a substance that is not fully reacted or bound to the magnetic particles, the solvent, by-products and contaminants, as well as a mixture of two or more of the described above.

Within the framework of the invention, a liquid may be a solution, in particular a reaction mixture of biomolecules and/or reagents and/or impurities.

In the following, a magnetic particle can generally be a particle in the micrometer or millimeter range. A magnetic particle can also be porous. In the following, a biomolecule may generally be bound to the surface of the magnetic particles via thiol groups and/or amino groups and/or hydroxy groups and/or carboxyl groups and/or carbonyl groups and/or ester groups and/or nitrile groups and/or amine groups and/or any other functional groups. A magnetic particle can also be a coated nickel particle or any other ferro- or paramagnetic particle. Magnetic particles typically have a diameter of about 1 micrometer. Within the framework of the invention, the term "about 1 micrometer" means 0.5 to 1.5 micrometers, in particular 0.7 to 1.3 micrometers, especially 0.9 to 1.1 micrometers.

The advantages of the device according to the invention and of the method according to the invention are as follows:

short process times due to faster flow-off
high yields
cleaner products
efficient and cost-effective
easy to automate
also for devices of reduced size
allows easy modification of existing machines
separation can be switched without moving the disposable (only with electromagnet)

In practice, the device and method can be used for post-ligation purification.

The magnet of the device according to the invention can be designed as a permanent magnet and/or as an electromagnet. While the shape of a permanent magnet influences the homogeneity of the magnetic field, the homogeneity of an electromagnet can be determined via the winding. Thus, the shape of the permanent magnet can ensure that the magnetic field is inhomogeneous to such an extent that the magnetic particles arrange themselves in a structured manner due to its influence. The term "arrange in a structured manner" may refer for example, to an arrangement in several spatially separated islands from which liquid can flow off well. If an electromagnet is used, however, a stronger magnetic field can be generated in places by a winding that is denser in places, so that an inhomogeneous magnetic field is also generated in which the magnetic particles arrange themselves in a structured manner.

The arrangement of the magnet may also be such that the magnet comprises a magnetically conductive module so that an inhomogeneous magnetic field acting on the magnetic particles located in the container is generated by the magnetically conductive module. The magnetically conductive module must therefore influence the field lines of a magnetic field of the magnet in such a way that the magnetic particles arrange themselves in a structure according to the invention. For this purpose, the magnetic field of the magnet can be amplified or attenuated by the magnetically conductive module at predeterminable points of the container, so that the magnetic particles arrange themselves increasingly in the amplified areas or they arrange themselves in the attenuated areas of the container in a reduced way. In this way, alternating partial areas can be generated in the container with an amplified or attenuated magnetic field. It is also conceivable that the magnetically conductive module amplifies the magnetic field of the magnet in predeterminable areas and attenuates it in the unamplified areas. The shape of the magnet can also be adapted in such a way that the magnetic field is amplified at predeterminable areas of the container and attenuated at unamplified areas.

In addition, the magnetically conductive module can be arranged as a component on the magnet or the magnetically conductive module can be designed as an integrated element of the magnet. The magnetically conductive module can thus be an attachment for the magnet and also an element, which is arranged between the container and the magnet. In a ring magnet, for example, a magnetically conductive module can be arranged as a smaller ring, with indentations or other deformations, between the container and the magnet.

In general, the magnetically conductive module can be arranged directly on the magnet or at a predeterminable distance from the magnet. The homogeneous magnetic field of the magnet is transformed into an inhomogeneous magnetic field by the magnetically conductive module.

The magnetically conductive module can be designed as a magnetically amplifying module and/or as a diamagnetic module. The magnetic field of the magnet is amplified in predeterminable areas of the container by the magnetically amplifying module and the magnetic field of the magnet is attenuated in predeterminable areas of the container by the diamagnetic module. The diamagnetic module could also be designed as a plurality of diamagnetic shields, which are arranged on the magnet in such a way that the magnetic field of the magnet in the container is shielded in places and thus weakened.

The diamagnetic module consists of a diamagnetic material, such as graphite, with a relative permeability of <1. The magnetically amplifying module consists of a ferromagnetic and/or paramagnetic material with a relative permeability >1. Typical ferromagnetic materials are for example iron, nickel and cobalt. Typical paramagnetic substances are for example alkaline earth metals. In an embodiment of the invention, a mixture of a diamagnetic module with a magnetically amplifying module can also be used, in which the module has different diamagnetic and ferromagnetic/paramagnetic subranges.

In practice, a shape of the magnet can be adapted to a shape of the container so that the container can be inserted into the magnetically conductive module. Of course, the shape of the magnetically conductive module can also be adapted to the container. In addition, the magnet may comprise a hole and/or an indentation for inserting the container. The magnetically conductive module may also comprise a hole and/or an indentation for inserting the container.

The container can be shaped in any way. In an embodiment of the invention, the container may be a multiwell plate, wherein the multiwell plate has a plurality of wells. A multiwell plate can in particular also be a microtiter plate. Particularly advantageously, the container may also comprise a capillary, in which the liquid with the magnetic particles is held by capillary forces and/or the liquid is removed by pressure.

A magnet can be arranged at a plurality of wells of the multiwell plate. In this way, the magnetic particles can be fixed in several wells at the same time.

The arrangement of the magnet can also be designed such that a second magnet is arranged on the magnet in such a way that the first magnetic field of the magnet can be influenced by the second magnetic field of the second magnet, such that an inhomogeneous magnetic field acting on the magnetic particles located in the container can be generated. If several permanent magnets are used as a second magnet, the permanent magnets can be arranged on the magnet in such a way that the magnetic field of the magnet is attenuated and/or amplified in some places. An electromagnet could also be used as a second magnet, which inhomogenizes the magnetic field of the magnet in the desired way with its second magnetic field.

In an embodiment of the invention, the arrangement of the magnet can also be designed such that the magnet has one or more notches so that an inhomogeneous magnetic field is generated by the notch of the magnet. A weaker magnetic field is generated in the container at the locations of the notches of the magnet, so that less or no magnetic particles collect at the locations of the notches.

In practice, the device may comprise an instrument for removing the liquid, so that the liquid can be removed from the container after immobilizing the biomolecules on the surface of the magnetic particles. The instrument for removing the liquid may be a pipette, a valve, compressed air or another suitable instrument.

According to the invention, a method for the reversible immobilization of biomolecules is further proposed. The method comprises the following steps. First the magnetic particles and a liquid with biomolecules are arranged in a container. Then the biomolecules are bound to the magnetic particles, in particular reversibly bound.

The magnetic particles with the immobilized biomolecules are fixed in the container in an inhomogeneous magnetic field generated by the arrangement of the magnet, so that the magnetic particles arrange themselves in a structured manner. Subsequently, the liquid is removed with an instrument for removing a liquid, wherein the liquid flows off from the magnetic particles by the structured arrangement of the magnetic particles, so that no or only little liquid residue remains in the container and on the magnetic particles. The biomolecules bound to the magnetic particles can be detached from the surface of the magnetic particles and then used further.

The method described above is preferably carried out with a device according to the invention.

According to embodiments of the invention, an apparatus for the automated processing of biomolecules comprising a device according to the invention is also proposed. In the apparatus for the automated processing of biomolecules, for example, a method according to the invention can be carried out. The advantage of such an apparatus is that the liquid with biomolecules and the magnetic particles can be fed into the container and removed from the container by suitable elements. In addition, the magnet position on the container can be changed if necessary, for example to remove the magnetic particles out of the container. Multiwell plates are typically used as containers in apparatuses for the automated processing of biomolecules.

BRIEF DESCRIPTION OF THE DRAWINGS

The invention will be explained in more detail hereinafter with reference to the drawings.

FIG. 2 is a schematic representation of various shapes of the magnet and the magnetically conductive module;

FIG. 3 is a schematic representation of another embodiment of a device for the reversible immobilization of biomolecules;

FIG. 6 is a schematic representation of a ring magnet with a magnetically conductive module as magnetically amplifying module and diamagnetic module.

DETAILED DESCRIPTION OF EMBODIMENTS

Figure 1:
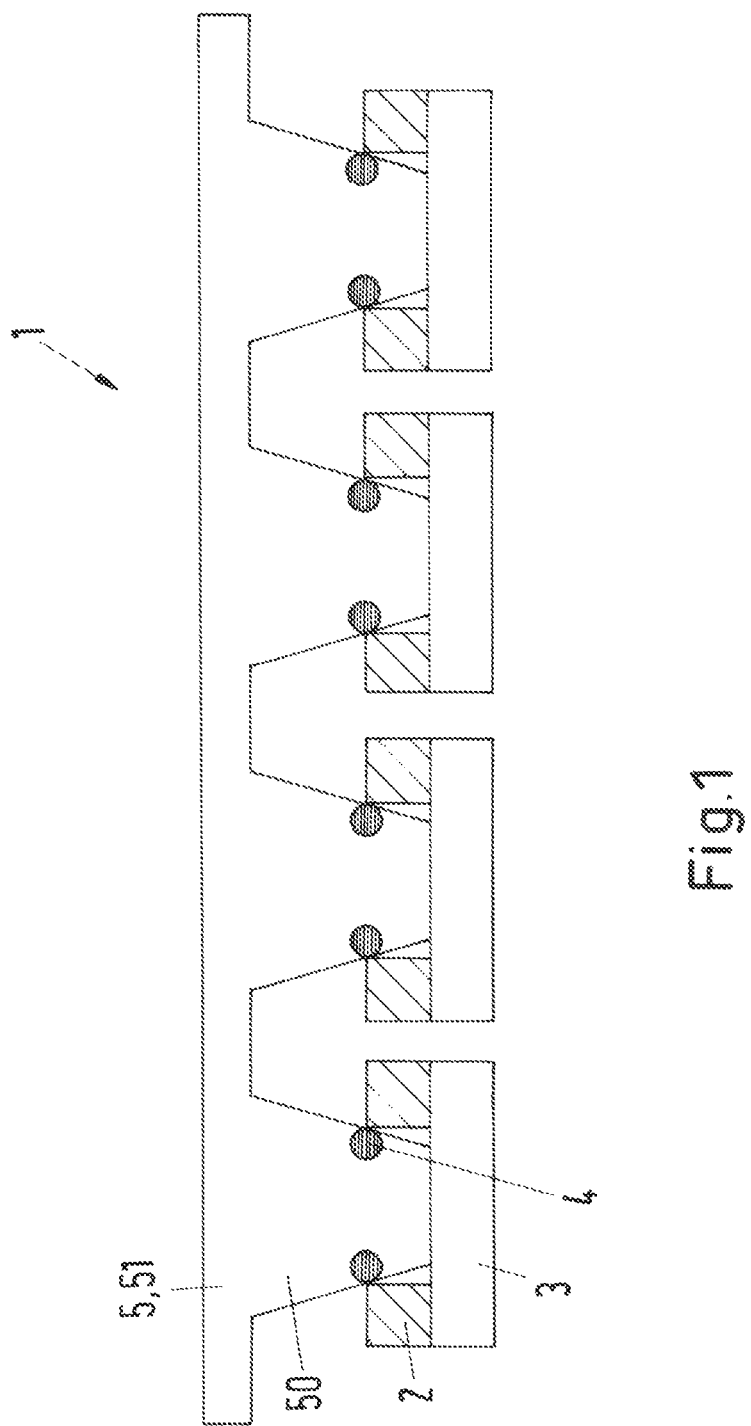
FIG. 1 is a schematic representation of a device for the reversible immobilization of biomolecules with a multiwell plate and a magnetically conductive module.

FIG. 1 shows a schematic representation of a device 1 for the reversible immobilization of biomolecules with a multiwell plate 51 and a magnetically conductive module 2. In the device 1 shown, the arrangement of the magnet 3 is configured with a magnetically conductive module 2. The magnetically conductive module 2 is arranged as an attachment on magnet 3 in such a way that it is located between magnet 3 and wells 50 of the multiwell plate 51.

Due to the arrangement of the magnet 3 with the magnetically conductive module 2 described above, the magnetic particles 4 arrange themselves in a structured manner in the container. In the operating state, after immobilization of the biomolecules on the surface of the magnetic particles, a liquid can be removed with an instrument for removing a liquid (not shown here) and the liquid can simply flow off between the structurally arranged magnetic particles.

FIG. 2 shows a schematic representation of various shapes of the magnet 3 and the magnetically conductive module 2. The magnet 3 can be designed as a crown-shaped magnet 201, as a wave-shaped magnet 202 and as a notched magnet 203, for example. Of course, the magnetically conductive module can also be crown-shaped, wave-shaped or with a notch. Due to the crown shape, the magnetic particles arrange themselves in several isolated islands. The number of islands of magnetic particles corresponds to the number of teeth of the crown. The magnetic particles would also arrange themselves in the same way in the wave shape. With a notch, however, the magnetic particles arrange themselves in two isolated islands.

FIG. 3 shows a schematic representation of another embodiment of a device 1 for the reversible immobilization of biomolecules. A container 5 is shown in which a liquid 6 with biomolecules is filled.

In the operating state, the biomolecules would be immobilized on the surface of the magnetic particles (not shown here). Subsequently, the liquid 6 would be removed from the container.

Furthermore, FIG. 3 shows that a magnet 3 with a magnetically conductive module 2 can be arranged on the container. Here, the magnetically conductive module 2 is designed as a crown-shaped attachment. Alternatively, a crown-shaped magnet 201 can be arranged on the container. Both arrangements shown have a shape which is adapted to the shape of the container 5 so that the container can be partially inserted into the magnet or into the magnetically conductive module.

Figure 4:
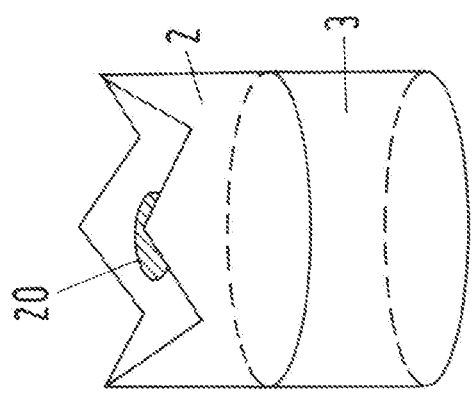
FIG. 4 is a schematic representation of a magnet with a magnetically conductive module in crown shape.

FIG. 4 shows a schematic representation of a magnet with a magnetically conductive module 2 in crown shape. Here, the magnetically conductive module 2 is designed as an attachment for the magnet 3. The magnetically conductive module 2 has a hole 20 into which a container can be inserted for fastening.

Figure 5:
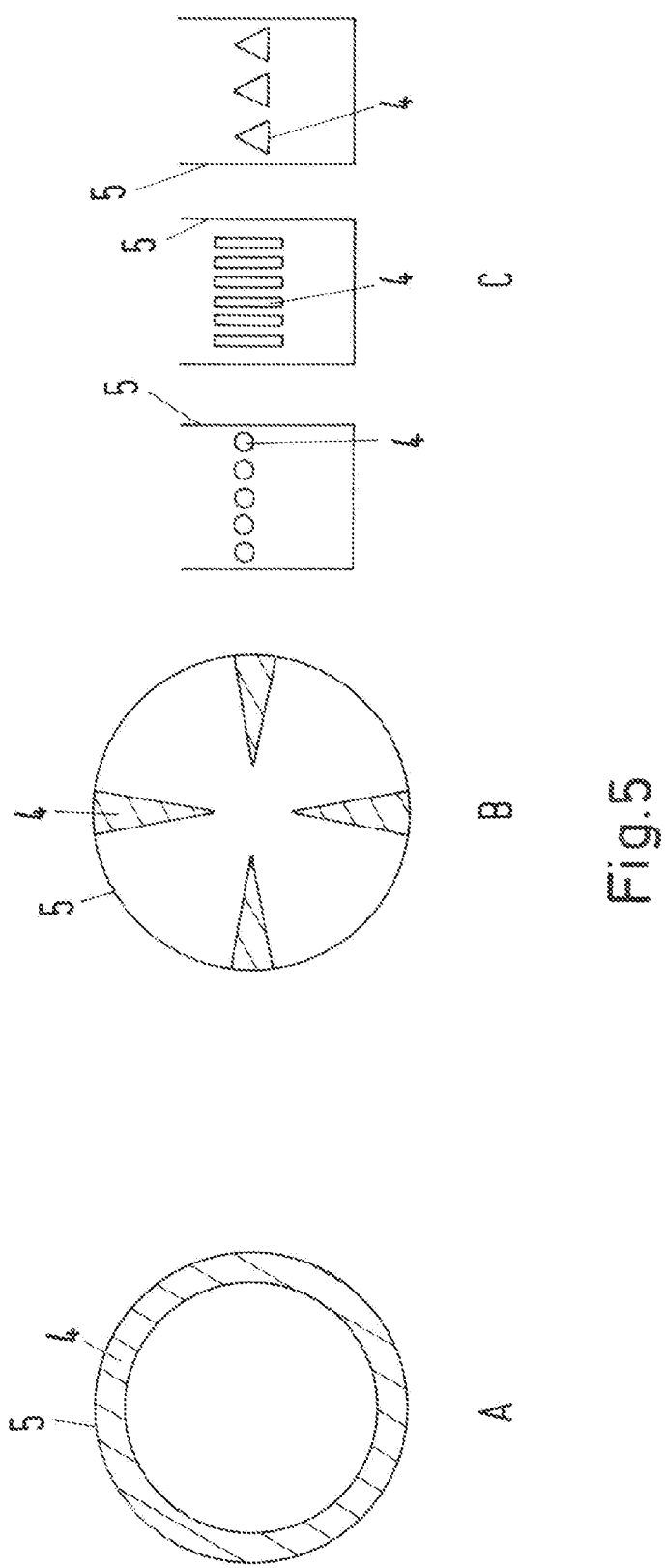
FIG. 5 is a schematic representation of the state of the art in comparison to the invention in view from above, as well as embodiments of the invention in side view.

FIG. 5 shows a schematic representation of the state of the art A in comparison to the invention B in view from above at the container 5, as well as embodiments of the invention C in side view of the container 5.

In the state of the art A, the magnetic particles 4 arrange themselves in a ring at the edge of the container 5 by the homogeneous magnetic field of the magnet. The liquid remains on this ring during removal, as it cannot flow off.

In the invention B, the magnetic particles 4 arrange themselves in a structured manner on the container wall by the inhomogeneous magnetic field of the magnet. By arranging the magnetic particles 4 in several isolated islands as shown here, the liquid can easily flow off between the magnetic particles 4.

In part C of FIG. 5, three embodiments of possible arrangements of the magnetic particles 4 in an inhomogeneous magnetic field according to the invention on the container wall of the container 5 are shown. An arrangement in several roundish islands is shown, as well as a groove-shaped and a pyramidal arrangement of the magnetic particles 4 are shown. All these arrangements are only exemplary and not restrictive. Only diverse possibilities are to be pointed out. In an inhomogeneous magnetic field according to the invention, magnetic particles can of course arrange themselves in any suitable structure, which allows a simplified flow-off of the liquid.

FIG. 6 shows a schematic representation of a ring magnet 3 with magnetically conductive module 2 as magnetically amplifying module and diamagnetic module.

In part A of FIG. 6, the magnetically conductive module 2 is a magnetically amplifying module. The magnetically amplifying module is configured as an insertion for a ring magnet 3 and is arranged between the ring magnet 3 and the container 5. Due to the magnetically amplifying module, the magnetic field of the ring magnet 3 is amplified more in areas without gap 23 and thus becomes inhomogeneous. The magnetic particles 5 thus arrange themselves structured on the wall of the container 5 between the gaps 23.

In part B of FIG. 6, the magnetically conductive module 2 is a diamagnetic module. The diamagnetic module is configured as an insertion for a ring magnet 3 and is arranged between the ring magnet 3 and the container 5. Due to the diamagnetic module, the magnetic field of the ring magnet 3 is attenuated more strongly in areas without gap 23 and thus becomes inhomogeneous. The magnetic particles 5 thus arrange themselves structured on the wall of the container 5 in the gaps 23.

The invention claimed is:

1. A device for reversible immobilization of biomolecules by magnetic particles, the device comprising:
   a container configured to be filled with a liquid containing biomolecules and magnetic particles, at least a part of the container defining a circumferential direction; and
   a magnet structure capable of being arranged on the container so that the magnetic particles arranged in the container, are configured to be fixed in the container;
   the magnet structure comprising a ring shaped magnet and a magnetically conductive module stacked vertically with respect to the ring shaped magnet, the magnetically conductive module having spaces between portions of the magnetically conductive module in the circumferential direction of the container so as to act more strongly on the magnetic particles in some areas and less strongly on the magnetic particles in others to generate an inhomogeneous magnetic field that causes the magnetic particles disposed in the container to become arranged on a container wall of the container in a plurality of isolated islands, such that the liquid is capable of flowing off between the plurality of isolated islands of the magnetic particles.

2. The device according to claim 1, wherein the magnetically conductive module is arranged on the ring shaped magnet or the magnetically conductive module is integrated with the ring-shaped magnet of the magnet structure.

3. The device according to claim 1, wherein the magnetically conductive module is a magnetically amplifying module or a diamagnetic module.

4. The device according to claim 1, wherein a shape of the magnet structure comprises a shape of the container, so that the container is capable of being inserted into the magnet structure.

5. The device according to claim 1, wherein the container is a multiwell plate.

6. The device according to claim 5, wherein the magnet structure is arranged at a plurality of wells of the multiwell plate.

7. The device according to claim 1, wherein the magnet structure comprises a hole or an indentation for inserting the container.

8. The device according to claim 1, wherein the conductive module is arranged on the ring-shaped magnet so that a first magnetic field of the ring-shaped magnet is capable of being influenced by a second magnetic field of the conductive module magnet, so that the inhomogeneous magnetic field acting on the magnetic particles disposed in the container is capable of being generated.

9. The device according to claim 1, wherein the magnet structure is a permanent magnet or an electromagnet.

10. The device according to claim 1, wherein the device comprises an instrument capable of removing the liquid.

11. The device according to claim 1, wherein
    the biomolecules are capable of being reversibly immobilized.

12. The device according claim 1, wherein the magnetically conductive module that has one of a crown-shape, a wave-shape and a notch.

13. A method for reversible immobilization of biomolecules, the method comprising:
    arranging magnetic particles and a liquid with biomolecules in a container;
    bonding the biomolecules to the magnetic particles;
    generating an inhomogeneous magnetic field with a magnet so that the magnetic particles arrange on a container wall of the container in a plurality of isolated islands, such that the liquid can flow off between the plurality of isolated islands of the magnetic particles;
    removing the liquid with an instrument for removing a liquid, the liquid flowing off from the magnetic particles between the plurality of isolated islands by the arrangement of the magnetic particles in several of the plurality of isolated islands;
    detaching the biomolecules from the magnetic particles; and
    operating the device according to claim 2 to carry out the method.

14. A method for reversible immobilization of biomolecules,
    the method comprising:
    arranging magnetic particles and a liquid with biomolecules in a container, at least a part of the container defining a circumferential direction;
    bonding the biomolecules to the magnetic particles;
    generating an inhomogeneous magnetic field with a magnet structure, the magnet structure comprising a ring shaped magnet with a magnetically conductive module stacked vertically with respect to the ring shaped magnet, the magnetically conductive module defining a space between portions of the magnetically conductive module in the circumferential direction of the container so as to act more strongly on the magnetic particles in some areas and less strongly on the magnetic particles in others so that the magnetic particles arrange on a container wall of the container in a plurality of isolated islands, such that the liquid can flow off between the plurality of isolated islands of the magnetic particles;
    removing the liquid with an instrument for removing a liquid, the liquid flowing off from the magnetic particles between the plurality of isolated islands by the arrangement of the magnetic particles in several of the plurality of isolated islands; and
    detaching the biomolecules from the magnetic particles.

15. The method according to claim 14, wherein the bonding includes reversibly bonding the biomolecules to the magnetic particles.

* * * * *